(12) United States Patent
Park

(10) Patent No.: US 6,682,495 B2
(45) Date of Patent: Jan. 27, 2004

(54) HORIZONTAL MOTION VIBRATING BED

(76) Inventor: Young-Go Park, #134-1301 Park Town Apartments, No. 55 Sunae-Dong, Bundang-Ku, Sungnam-Si, Kyounggi-Do, 463-728 (KR)

( * ) Notice: Subject to any disclaimer, the term of this patent is extended or adjusted under 35 U.S.C. 154(b) by 0 days.

(21) Appl. No.: 10/034,259

(22) Filed: Jan. 3, 2002

(65) Prior Publication Data

US 2003/0032902 A1 Feb. 13, 2003

(30) Foreign Application Priority Data

Aug. 9, 2001 (KR) .......................... 2001-48086

(51) Int. Cl.[7] .................................................. A61H 7/00
(52) U.S. Cl. ............................ 601/98; 601/101; 601/84
(58) Field of Search .......................... 601/46, 97, 98, 601/101, 102, 90–93, 85–87, 49–51, 53, 54; 5/33, 108, 109

(56) References Cited

U.S. PATENT DOCUMENTS

| | | | | |
|---|---|---|---|---|
| 1,567,819 A | * | 12/1925 | Stebbins ........................ 5/261 |
| 2,999,496 A | * | 9/1961 | Le Roy Parson ............... 29/29 |
| 3,656,195 A | * | 4/1972 | Leahey ........................... 5/109 |
| 3,882,556 A | * | 5/1975 | Accurso ......................... 5/108 |
| 5,404,603 A | * | 4/1995 | Fukai et al. .................... 5/609 |
| 5,520,614 A | * | 5/1996 | McNamara et al. .......... 601/24 |
| 5,708,996 A | * | 1/1998 | Marenco ..................... 362/338 |
| 6,431,646 B1 | * | 8/2002 | Longoria ........................ 5/108 |

FOREIGN PATENT DOCUMENTS

| | | |
|---|---|---|
| JP | 60-6525 | 1/1985 |
| JP | 08-112323 | 5/1996 |

* cited by examiner

*Primary Examiner*—Danton D. DeMille
*Assistant Examiner*—Quang D Thanh
(74) *Attorney, Agent, or Firm*—Robert E. Bushnell, Esq.

(57) ABSTRACT

A vibrating bed comprising a basic bed having a bed frame, casters secured on the basic bed, a lateral vibrating bed plate movably ridden on the casters, a mechanism for reciprocally moving the vibrating bed plate with respect to the bed frame, a connecting rod adjusting device and tension coil springs for dampening the vibrations of the vibrating bed plate as the vibrating bed plate reaches a predetermined horizontal, or lateral, position.

2 Claims, 4 Drawing Sheets

HORIZONTAL MOTION VIBRATING BED

BACKGROUND OF THE INVENTION

1. Technical Field

The present invention relates to a bed more particularly a vibrating bed which vibrates laterally, i.e., horizontally, by itself and vibrates wholly a human body on it. The vibrating bed is used for escalating extra pleasure of a couple who are making love on it while it is vibrating, as a bed for fast releasing fatigue of a tired person who is on it while it is vibrating, also as a bed for expediting sleeping of an sleeplessness person who is on it while it is vibrating, and as an usual bed for every one who is on it while it is not vibrating.

2. Prior Art

The prior art of the vibrating bed used as a pleasure bed is not available except for modifying the quality of its mattresses. That of the vibrating bed used as a conventional bed is as same as hereinabove.

That of the vibrating bed used as a bed has two instances: one is Japanese "Utility model opening Gazzete""Showa 60-6525" that the bed vibrates a human body partly, not the whole body simultaneously; the other one is also Japanese "Patent Gazzete" "HEISEI 8-112323" regarding a massage device that vibrates a body.

SUMMARY OF THE INVENTION

It is an object of the present invention to provide a love making couple on it with escalated extra pleasure by vibrating whole bodies caused by the lateral vibration of the whole bed.

It is another object of the present invention to provide a tired person with fast fatigue release by expediting the blood circulation function by the vibration of the whole body simultaneously caused by the bed vibration.

It is further object of the present invention to help an insomniac person to go to sleep by vibrating the whole body simultaneously caused by the bed vibration.

It is still further object of the present invention to provide a person with a conventional bed while it is not vibrating.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference numerals indicate the same or similar components, and wherein:

FIGS. 4 and 4A together form a perspective view of the second embodiment of the present invention with enlarged detail view of the tension coil spring device;

DETAILED DESCRIPTION OF THE EMBODIMENTS

Figure 1:
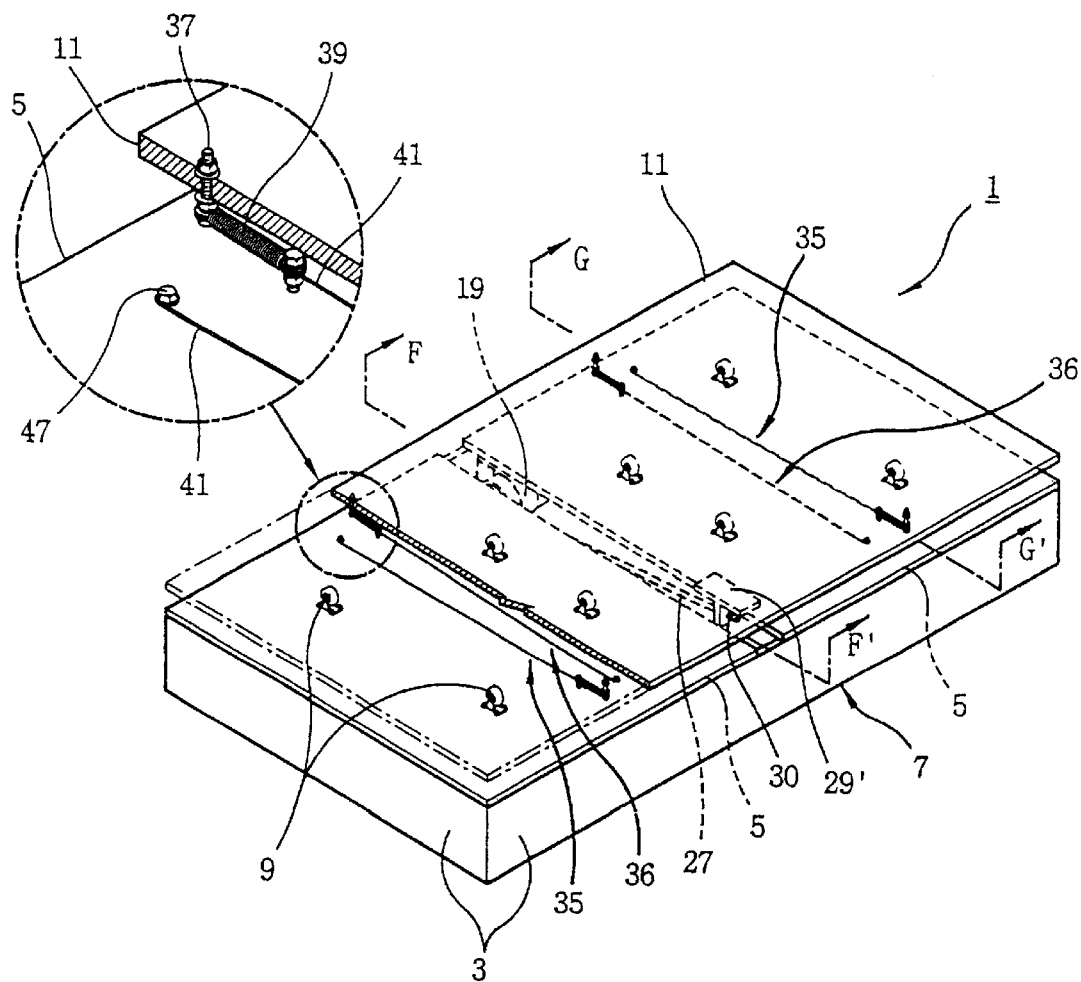
FIG. 1 is a perspective view of the first embodiment of the present invention with an enlarged detail view of the tension coil spring device.

The present invention, the vibrating bed comprises four major parts and two minor parts; the first major part of them, a vibrating bed plate (11) which is 10 mm less than the size of the conventional bed, and which is movably floated on second major parts, i.e., floating means, represented by plural casters (9) which are laterally secured on the third major part, a basic bed (7) consisting oaf four sided plate (3) which is conventional bed sized square shape and of which height is 30–50 cm (12–20 inches) and a basic bed plate (5) which is solidly secured to the four sided plate (3) at its top side and cut away its longitudinal mid-portion for a connecting rod (27) passage space set forth hereinafter, and the basic bed (7) could be the frame of the conventional bed.

Figure 2:
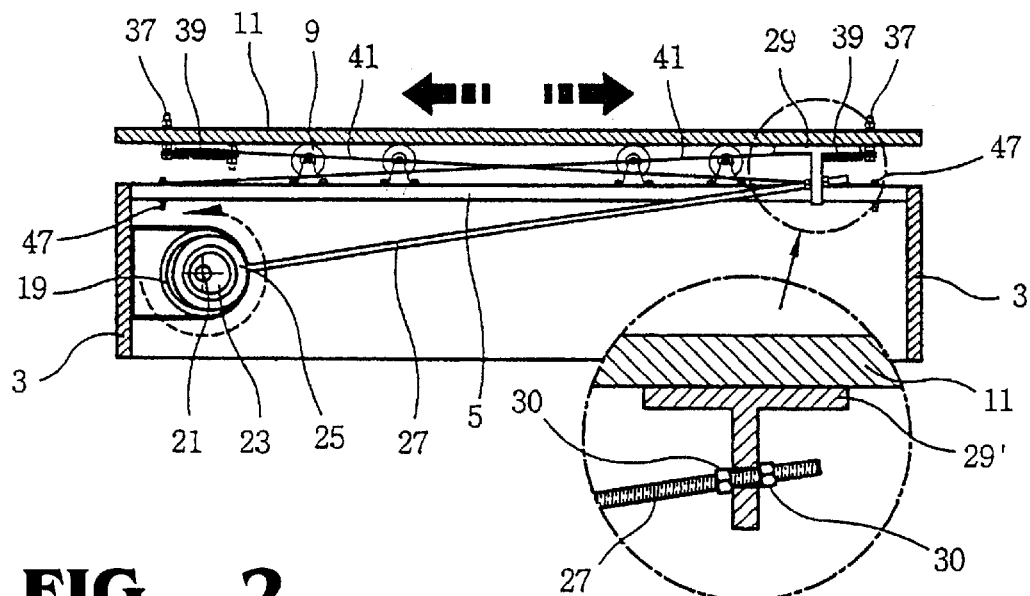
FIG. 2 is a sectional view- taken on line F–F' of FIG. 1.

The fourth major part, a rotary reciprocating mechanism is connected between the vibrating bed plate (11) and the four sided plate (3) of the basic bed (7), which comprises a variable speed motor (19) attached to the four sided plate (3) or basic bed plate (5), and as shown in FIG. 2, a motor shaft (21), an eccentric crank bushing (23), a bearing (25), a connecting rod (27) which is threaded at its one end, connecting rod adjusting nuts (30), and a "T" shape piston bracket (29) which is bolted to the vibrating bed plate (11).

The first minor part, dampening spring devices (35) (36) are hooked between both lateral ends of the vibrating bed plate (11) and basic bed plate (5), for smoother vibration, that means that inertia force of the vibrating bed plate (11) and body on it, are compensated, i.e., dampened, at the top dead point of the crank by the tension coil springs (35) while the other tension coil springs (36) are far most compressed. That also means that the motor shaft is prevented from jerked while vibrating the plate (11) which consequently saves the motor from damage. Another minor part is a connecting rod adjusting device, which is involved in the rotary reciprocating mechanism, comprising a connecting rod (27) with its one end threaded, a pair of connecting rod adjusting nuts (30), and a "T" shaped piston bracket (29), which adjusts the length of the connecting rod (27), i.e., adjusts the relative position including neutral position of the vibrating bed plate (11) to the basic bed plate (5) against the pair of tension coil springs (35) (36) described hereinafter.

Embodiment 1

Referring to the drawings, as shown in the FIGS. 1 and 2, the vibrating bed plate (11) is movably and floatably ridden on the plural casters (9), which are laterally secured on the basic bed plate (5) which is attached to the top side of the four sided plate (3).

A variable speed electric motor (19) of the rotary reciprocating mechanism is mounted on the four sided plate (3) at its internal lateral middle part as shown. The motor shaft (21) is inserted into an eccentric crank bushing (23), as shown in FIG. 2, which is also inserted into a bearing (25) in which a connecting rod (27) is also inserted. The connecting rod (27) is threaded at one end. The threaded end of the connecting rod (27) is inserted into a hole of a vertical plate of the "T" shaped piston bracket (29) which is bolted to a longitudinal middle part, lateral end, opposite side of the motor (19), and under side of the vibrating bed plate (11) so that the variable speed motor (19) makes the vibrating bed plate (11) reciprocate, that is, to vibrate laterally.

The degree of insertion of the threaded end of the connecting rod (27) for adjusting its length determines the relative position, including neutral position, of the vibrating plate (11) to the basic bed plate (5) against the pair of tension coil spring devices (35) and (36) described hereinafter, because the biased relative position of the vibrating bed plate (11) off the neutral position against the pair of tension coil springs 35 and 36 makes noise.

When the neutral position is searched and determined, the threaded end shall be tightened to the "T" shape piston bracket (29) by both side connecting rod adjusting nuts (30).

Figure 3:
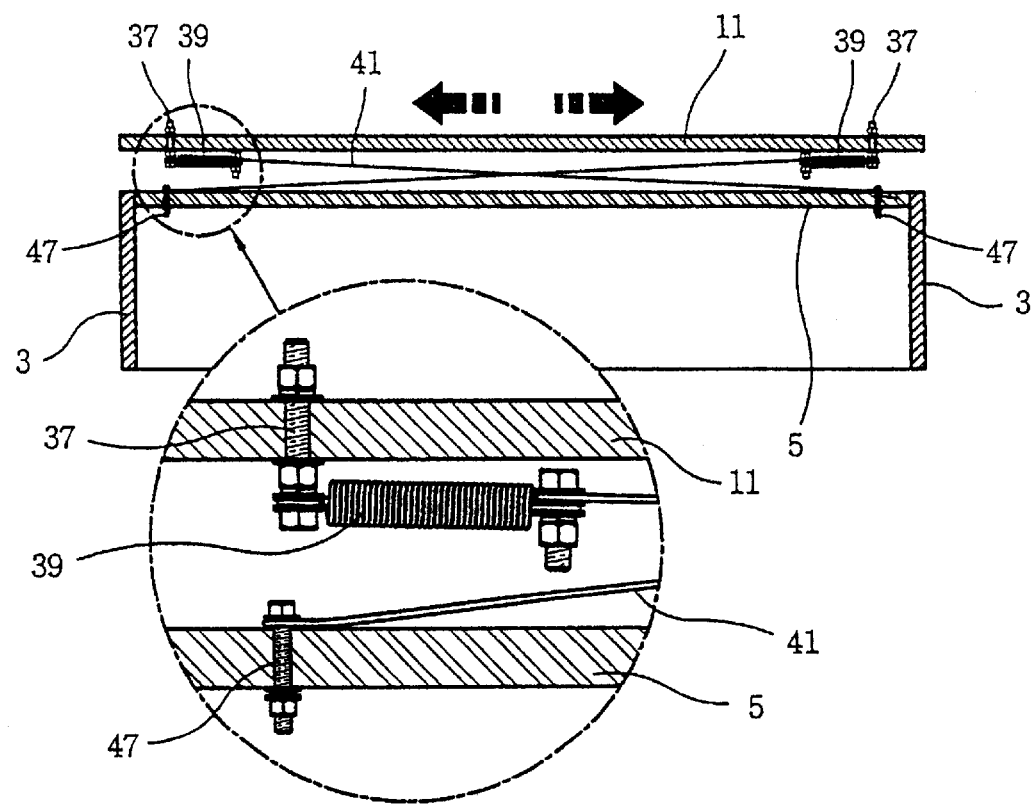
FIG. 3 is a sectional view taken on line G–G' of FIG. 1.

In order to make the vibration of vibrating bed plate (11) smoother and extend the motor life, the extended tension coil spring device (35) force compensates the inertia force of the vibrating bed plate (11) and body on it at one top dead point of the crank while the other spring device (36) has the weakest tension force. The pair of tension coil spring devices (35) (36) connect one lateral end of the vibrating bed plate (11) and the other lateral end of the basic bed plate (5), comprise, as shown in the FIG. 3, vibrating bed plate connecting bolts (37), tension coil springs (39), spring connecting hooks (41), and basic bed plate connecting bolts (47), where the tension coil spring (39) and the spring connecting hook (41) are connected to each other, the tension coil spring is connected to the vibrating bed plate (11) by the vibrating bed plate connecting bolt (37), and the spring connecting hook (41) is fastened to the basic bed plate (5) by basic bed plate connecting bolt (47).

Embodiment 2

In the embodiment 1, a variable speed driving motor (19) which actually comprises reduction gears, attached to the four sided plate (3) is excluded and replaced by a variable speed driving motor (19') with speed reducing pulleys (22) (26) and belt (24) mechanism, instead of the reduction gears, for delivering reduced motor speed to the vibrating bed plate (11).

Figure 4:
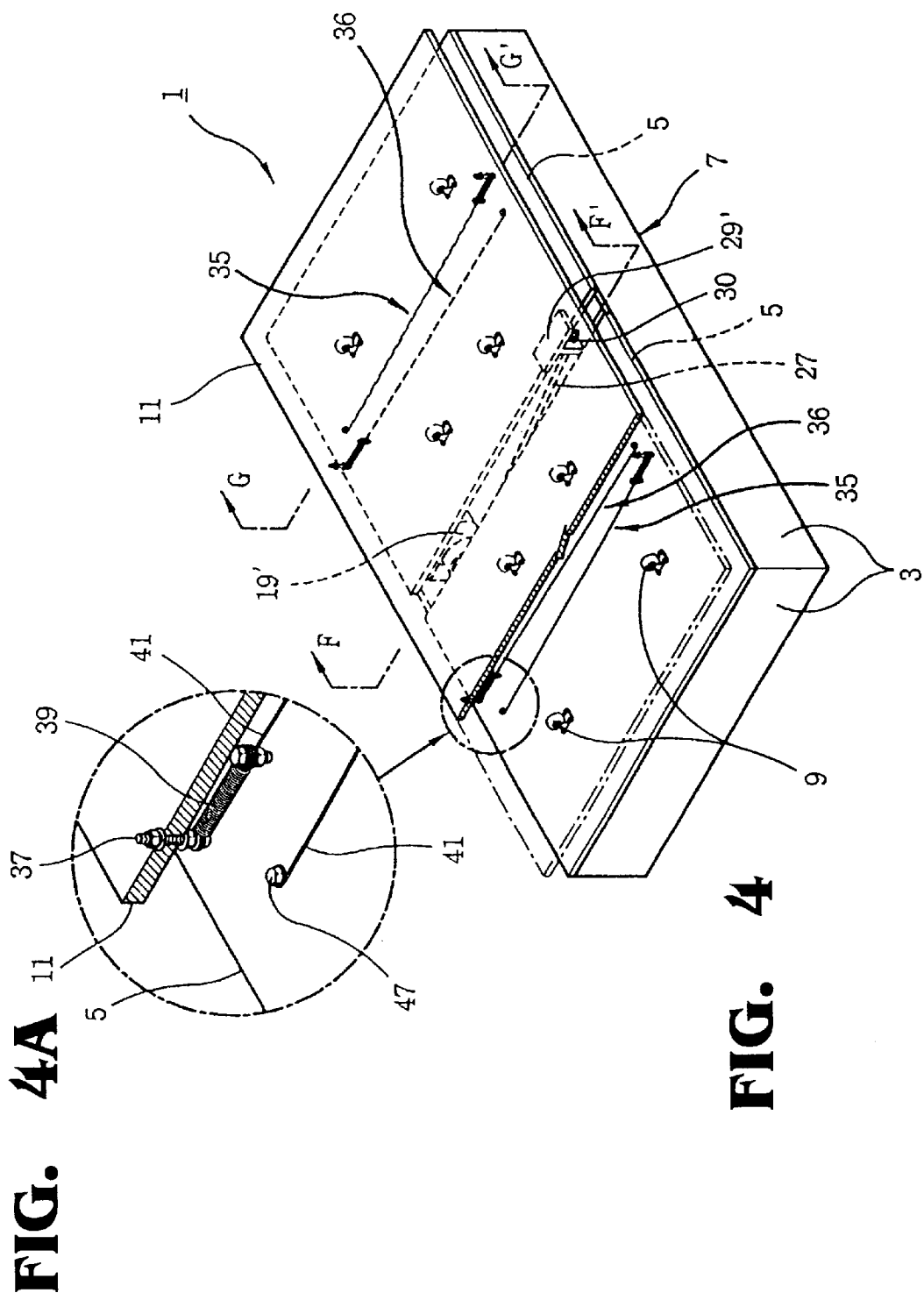
Figure 5:
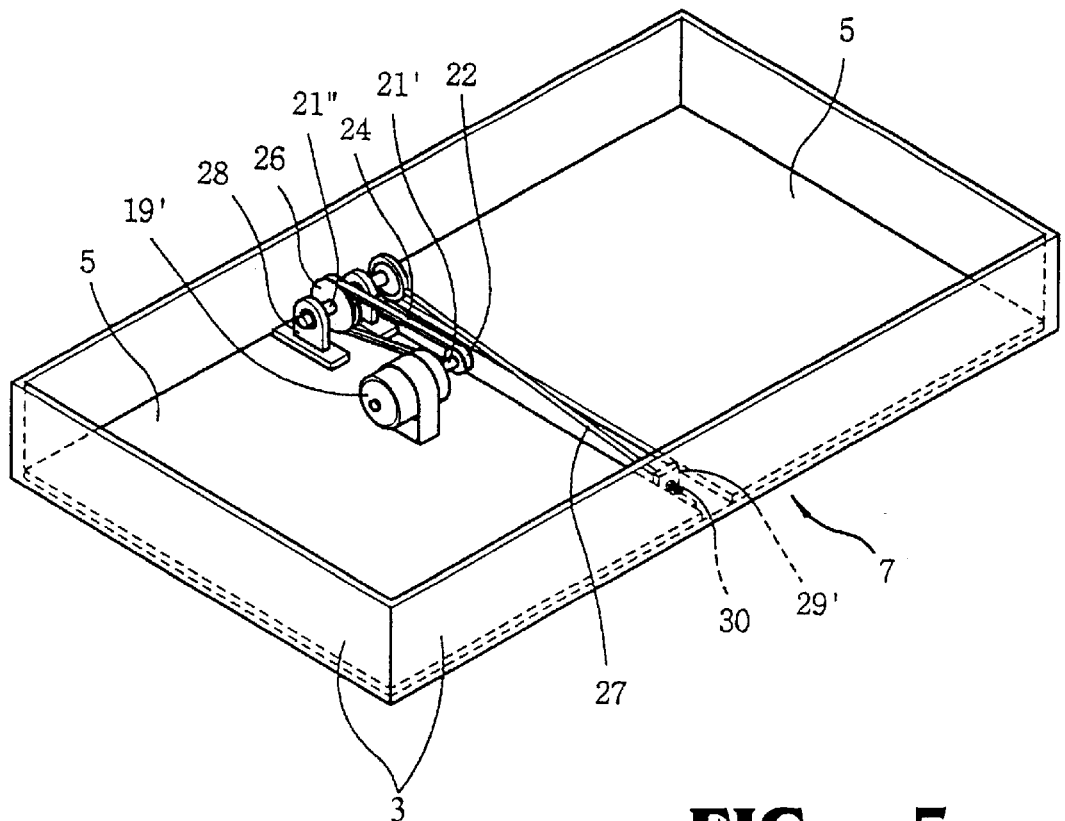
FIG. 5 is a perspective view of the pulleys and belt mechanism attached on the bottom of the basic bed plate according to the second embodiment.

For vibrating the vibrating bed plate (11), as shown in the FIGS. 4 through 5, a variable speed motor (19') is attached on the bottom of the basic bed plate (5). A smaller pulley (22) is secured on the shaft (21') of the motor (19'). A belt (24) is hooked on the smaller pulley (22) and another larger pulley (26) which is secured on a pulley shaft (21") so that the belt (24) delivers motor power to the pulley shaft (21") which is rotatably secured on the bottom of the basic bed plate (5) by a couple of bearing brackets (28).

Figure 6:
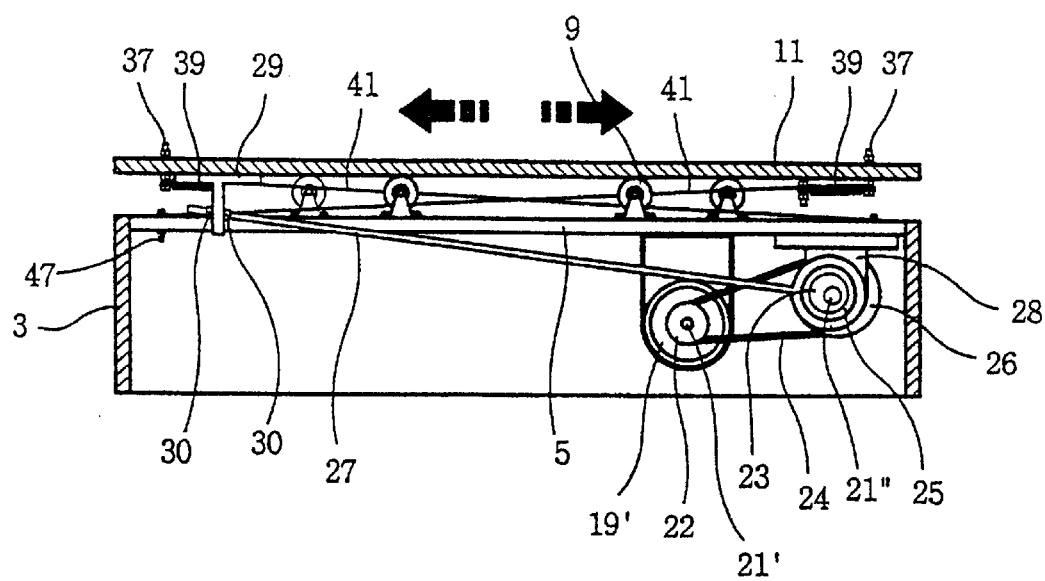
FIG. 6 is a sectional view take on line F–F' of FIG. 4.

At the end of the pulley shaft (21"), an eccentric crank bushing (23) is inserted, as shown in FIGS. 5 and 6.

Effects

As set forth hereinabove, the vibrating bed has four effects as described hereinafter. First, when a couple are making love on it, and the upper partner wants lower partner to make more severe body movements and vibration for more escalated pleasure, though, the lower partner is unable to move or vibrate by oneself because the lower partner is pressed by the weight of the upper partner, the vibrating bed assists the lower partner is moving.

When a couple are on the vibrating bed, they are wholly vibrated laterally by the vibrating vibrating bed.

The friction between the piston and cylinder of both partners become more pressed and frequently vibrated due to the inertia force reaction/lag between both partners vibrated by the vibration of the vibrating bed, which in turn generates more and extra pleasure for both partners.

Second, when a tired person uses the present invention for 20–30 minutes, the fatigue will be quickly eased because the body vibration generated by the vibration of the vibrating bed, expedites the blood circulation of the body.

Third, a person who is unable to sleep fast, can sleep easily when he/she uses the present invention.

Fourth, while the vibrating bed is not in operation it could be used as a conventional bed.

It could be truly said that the present vibrating bed will provide a human being with one dimension higher pleasure and happiness.

Because the present invention, the vibrating bed, vibrates the human body with relatively high frequencies, the body's blood vessels are also shaken and vibrated.

How to use

The vibrating bed vibrating by itself makes whole human bodies on it to vibrate simultaneously. Accordingly, the bodies on it received vibration from it, vibrate wholly and simultaneously expedite blood circulations, manipulate the bone positions, exercise the internal organs of the bodies, and to exercise and relax the muscles to release their stress.

Consequently, the users must select the time period used, the shape of the bodies on it to receive the vibrations, and the frequency of the vibration.

Especially concerning the frequencies, it must be selected carefully because human body wholly and partially has its own resonance frequencies like critical speed in the mechanical field at which human feels maximum pleasure and happiness. The vibrating bed is simply an exercising apparatus that provides human body with physical exercises.

The purpose of the use are for love making, fast fatigue recovery, inviting fast sleep and relaxing, preventing the decubitus ulcer of long patient on a bed and usual conventional bed.

The using procedure is as followings:

(1) Select timer switch for time period;
(2) Power switch on;
(3) Select the frequency by adjusting the motor speed controller for user's optimum best feeling frequency by trial and error (trying several times); The range of the frequencies varies (a) around 280–350 rpm for love making; (b) around 100–160 rpm or less for inviting fast sleep and relaxing; (c) around 280–350 rpm for expediting the recovery from fatigue, (mainly legs and arms exercises); (d) around 160–200 rpm for exercising internal organs; and (e) when preventing decubitus ulcer for bed ridden patients, 90–100 rpm for continuous vibrating and 200–220 rpm for 5 minutes intermittent vibrating every 30 minutes;
(4) Aged people could use it 2 hours after every meal for 20–30 minutes or more and whenever they want to. Any one could use it also 2 hours after every meal for 20–30 minutes, or more;
(5) The shape of the body receiving vibrations are upright laying down, right and left lateral laying down, and sitting on it like on a bench. The time period allocation for the shapes of the body for the fatigue recovery and relaxing, for instance, are upright shapes for 24 minutes, right and left lateral shape for 2 minutes respectively, and sitting shape on it for 2 minutes, in other words the allocation ratio will be 24:2:2:2. Warning: the lateral shape shall not be more than 2 minutes;
(6) Use it as a conventional bed while it is not vibrating;
(7) Especially, when controlling, and preventing hypertension; use 280–350 frequencies for first 20–30 minutes, and 160–200 frequencies for second 20–30 minutes in the early morning after bed and late night before bed twice a day or more.
(8) Warning: The pregnant ladies are prohibited to use the vibrating bed while it is vibrating.

Although the preferred embodiments of the present invention have been described, it will be understood by those skilled in the art that the present invention should not be limited to the described preferred embodiment. Rather, various changes and modifications can be made within the spirit and scope of the present invention, as defined by the following claims.

What is claim is:

1. A lateral motion vibrating bed comprising:

a vibrating bed plate movably ridden on a plurality of casters which are laterally secured on a basic bed plate of a basic bed, said basic bed consisting a four sided plate and said basic bed plate, which is solidly secured at the top of said four sided plate, and a central part of said basic bed plate is cut away for providing a connecting rod passage space;

a rotatory-reciprocating mechanism that connects said four sided plate of said basic bed to said vibrating bed plate, said mechanism comprising a variable speed motor bolted to a central part of said four sided plate, a shaft, an eccentric crank bushing, a connecting rod for connecting said mechanism to said vibrating bed plate, a pair of connecting rod adjusting nuts, and a T-shaped bracket secured on an under side of said vibrating bed plate;

a pair of opposite direction tension coil spring devices that connect said vibrating bed plate to said basic bed plate for compensating the inertia force of the vibrating bed plate and a user's body weight on said vibrating bed plate, each of said devices comprising a vibrating bed plate bolt, a tension coil spring, a spring connecting hook, and a basic bed plate connecting bolt.

2. A lateral motion vibrating bed as claimed in claim 1, wherein the bed further includes a speed reducing pulleys and belt mechanism that comprises a small pulley, a belt, a large pulley, a pair of bearing brackets, and a pulley shaft, and wherein said motor and bearing brackets are attached on a bottom of said basic bed plate and said pulley shaft is inserted by said eccentric crank bushing.

* * * * *